US007241417B2

(12) United States Patent
Lee et al.

(10) Patent No.: US 7,241,417 B2

(45) Date of Patent: Jul. 10, 2007

(54) ASSAY DEVICE

(75) Inventors: Martin Jerome Lee, Jerusalem (IL); Zvi Greenberg, Rehovot (IL); Eitan Rogel, Haifa (IL)

(73) Assignee: Savyon Diagnostics Ltd., Ashdod (IL)

( * ) Notice: Subject to any disclaimer, the term of this patent is extended or adjusted under 35 U.S.C. 154(b) by 0 days.

(21) Appl. No.: 11/188,799

(22) Filed: Jul. 26, 2005

(65) Prior Publication Data

US 2006/0024843 A1 Feb. 2, 2006

Related U.S. Application Data

(60) Provisional application No. 60/591,964, filed on Jul. 29, 2004.

(51) Int. Cl.

| | |
|---|---|
| ***G01N 21/00*** | (2006.01) |
| ***G01N 31/22*** | (2006.01) |
| ***G01N 15/06*** | (2006.01) |
| ***G01N 33/53*** | (2006.01) |
| ***G01N 1/10*** | (2006.01) |
| ***C12Q 1/68*** | (2006.01) |
| ***C12Q 1/00*** | (2006.01) |
| ***B32B 5/02*** | (2006.01) |
| ***C12M 1/00*** | (2006.01) |
| ***C12M 1/34*** | (2006.01) |
| ***C12M 3/00*** | (2006.01) |

(52) U.S. Cl. ........................... 422/58; 422/50; 422/55; 422/56; 422/68.1; 422/101; 422/103; 422/104; 435/4; 435/7.1; 435/283.1; 435/287.1; 435/287.2; 435/287.6; 435/288.7; 436/180

(58) Field of Classification Search ................. 422/50, 422/55, 56, 58, 68.1, 101, 103, 104; 435/4, 435/7.1, 283.1, 287.1, 287.2, 287.6, 288.7; 436/180

See application file for complete search history.

(56) References Cited

U.S. PATENT DOCUMENTS

| | | | | |
|---|---|---|---|---|
| 4,769,333 | A | 9/1988 | Dole et al. | |
| 4,943,522 | A | 7/1990 | Eisinger et al. | |
| 5,427,739 | A | 6/1995 | Meserol et al. | |
| 5,489,414 | A | 2/1996 | Schreiber et al. | |
| 5,602,040 | A | 2/1997 | May et al. | |
| 5,817,522 | A | 10/1998 | Goodman et al. | |
| 6,372,516 | B1 * | 4/2002 | Sun | 436/518 |
| 6,485,982 | B1 | 11/2002 | Charlton | |
| 2002/0004245 | A1 | 1/2002 | Chandler | |
| 2002/0173047 | A1 | 11/2002 | Hudak et al. | |
| 2005/0208677 | A1 * | 9/2005 | Owens et al. | 436/514 |

* cited by examiner

FOREIGN PATENT DOCUMENTS

WO WO 94/29696 A1 12/1994

*Primary Examiner*—Long V. Le
*Assistant Examiner*—Jacqueline A. DiRamio
(74) *Attorney, Agent, or Firm*—Browdy and Neimark, PLLC

(57) ABSTRACT

A device for carrying out a lateral flow assay on a sample comprising: (a) a sample containing unit comprising a sample container, said sample container being closed off at one end by a bottom wall, said bottom wall having a hole sealed by a plug; and (b) a housing located under said sample container and capable of holding a test strip, said sample containing unit and said housing being coupled so as to allow rotation one relative to the other, said housing comprising a cutting arrangement capable of cutting said plug; wherein rotation of said sample containing unit and said housing one relative to the other results in said cutting arrangement cutting said plug, thereby unplugging the hole in said bottom wall. Also disclosed is a method for determining the presence or absence of an analyte in a sample, using the device.

15 Claims, 6 Drawing Sheets

ASSAY DEVICE

FIELD OF THE INVENTION

This invention relates to an assay device and to a method using the device.

BACKGROUND OF THE INVENTION

Many devices have been described which may be used to carry out detection assays such as diagnostic immunoassays. Some of these devices are based on the principle of lateral flow, that is, the flow of a liquid along a solid phase by capillary and other forces.

Examples of prior art patents include U.S. Pat. Nos. 4,943,522, 5,427,739, 5,602,040, 6,485,982, 6,555,390, 6,565,808 and WO 94/29696.

SUMMARY OF THE INVENTION

The present invention provides a device for carrying out a lateral flow assay on a sample comprising:

(a) a sample containing unit comprising a sample container, the sample container being closed off at one end by a bottom wall, the bottom wall having a hole sealed by a plug; and (b) a housing located under said sample container and capable of holding a test strip, said sample containing unit and said housing being coupled so as to allow rotation one relative to the other, said housing comprising a cutting arrangement capable of cutting said plug;

wherein rotation of said sample containing unit and said housing one relative to the other results in said cutting arrangement cutting said plug, thereby unplugging the hole in said bottom wall.

The device of the invention enables the following procedures: (a) application of various types of biological specimens; (b) extraction of soluble materials, including the specific analyte of interest, in existing or added solutions; (c) providing conditions for any kind of sample pre-treatment, i.e. diluting, mixing, and so on; (d) housing a test strip upon which the detection process of the analyte takes place; (e) conveying solutions onto the test strip to commence the detection process; (f) providing the proper conditions for the immuno-chromatographic lateral flow-based detection assay to occur; and (g) viewing clearly the test results.

The cutting arrangement may be any means capable of removing the plug which seals the hole in the bottom wall of the sample container as a result of the rotation of the sample containing unit relative to the housing. One non-limiting example is a hole in the housing having a cutting edge, as described below. However, other cutting means are included within the scope of the invention, such as a straightedge.

The test strip which may be used with the device may be designed and manufactured as is well known in the art. For example, the test strip may comprise a sample application pad to receive the sample, and a detection zone capable of specifically detecting the analyte. The detection zone may be capable of detecting one or a plurality of analytes. The device may be designed to receive one or a plurality of test strips, which may be placed in the same or in different directions in the device. The housing may comprise a plurality of base supports for receiving a plurality of test strips. It is also possible to combine multiple devices side by side in a system for carrying out a lateral flow assay on one or more samples.

The device is designed to be used with all currently known types of specimens, and thus, enables usage of different sample collection vehicles, such as swabs, spoons, sticks, and so on. Accordingly, the analyte may be an antigen as well as an antibody. However, the analyte must be dissolved in a fluid state prior to being assayed. Thus, a solid or semi-solid sample containing the analyte must be first diluted with an appropriate extracting or diluting solution in order to extract the analyte into a fluid state. These options imply the possibility of introducing some changes in the following described components, especially in the sample containing component, in accordance with different affecting factors, like the nature of specimen, solution volume needed for a particular assay, the type of sample pre-treatment, and so on. These modifications may include addition of longitudinal ribs along the inner wall of the sample container to enhance mixing efficiency by causing turbulence during mixing, a filtering member to filter the sample prior to its reaching the test strip to prevent blocking of flow on the strip, etc.

The device is intended to be used as a test device for home, doctor's clinic or professional laboratories. In one preferred embodiment, the device is used in a vaginal yeast diagnostic test. In another preferred embodiment, it is used in a pregnancy test.

One or more of the following features are particularly important for the proper operation of the device of the invention:

a. The relative positions of the aperture and the conic hole in the bottom of the bore in the upper part of the strip housing component.

b. The dimensions of the hole in the bottom of the sample container and the aperture in the bottom of the bore, which should correspond to the volume of the tested fluid, the viscosity of this fluid, and the dimensions and capacity of the strip.

c. The position of the aligned holes after rotation of the sample containing unit, relative to the sample application pad of the test strip.

d. The amount and location of the pressure applied on the strip by the pressing bars and pins after assembling the upper and bottom parts of the strip housing component in order to ensure uniform flow in the strip.

e. The rotary mechanism of slicing off the plug in the bottom of the sample-containing unit together with alignment of the resulting opening with the aperture, thereby allowing the conveying of the sample to the test strip, without causing any interference in the strip function.

In one embodiment of the device of the invention, the device comprises a rotary control mechanism which comprises a limiting groove, a limiting protrusion, and notches on the sample-containing unit and the strip housing component, which are intended to operate the device in a constant, precise and indicative way, thereby reducing the possibility of error or misuse.

Also provided by the invention is a method for determining the presence or absence of an analyte in a sample, using the device of the invention and a test strip, the test strip comprising a detection zone capable of specifically detecting the analyte, the method comprising:

(a) introducing the sample into the sample container;

(b) if necessary, treating the sample so as to extract the analyte into a fluid state;

(c) rotating the sample container with respect to the housing, thereby slicing off the plug in the bottom wall of the sample container;

(d) waiting a predetermined amount of time to allow the sample to reach the detection zone in the test strip; and (e) viewing the results on the test strip, the results indicating the presence or absence of the analyte in the sample.

In a preferred embodiment, the method is an immunoassay, preferably a lateral flow immunoassay. Examples of types of analytes which may be determined using the method of the invention include vaginal yeast and pregnancy hormones.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF AN EMBODIMENT OF THE INVENTION

Description of the Device

Figure 1:
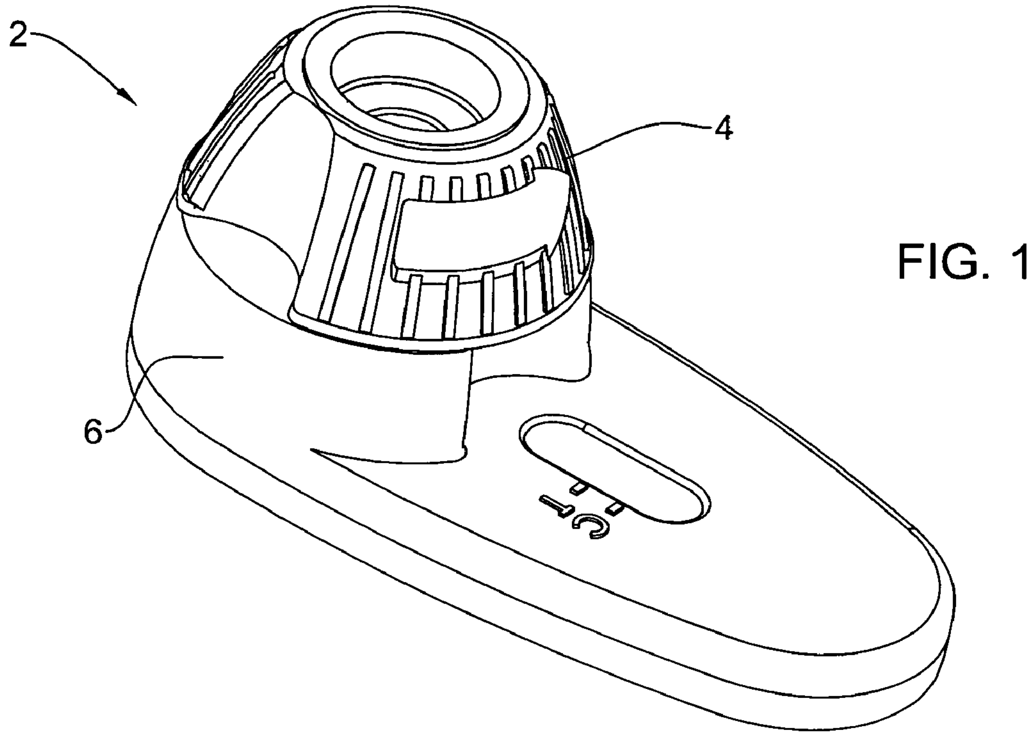
FIG. 1 is an overall view of one embodiment of the invention.

FIG. 1 illustrates one embodiment of the device of the invention, generally referred to as (2), which includes a sample containing unit (4) and a laterally oriented housing component (6), which houses the test strip.

Figure 2:
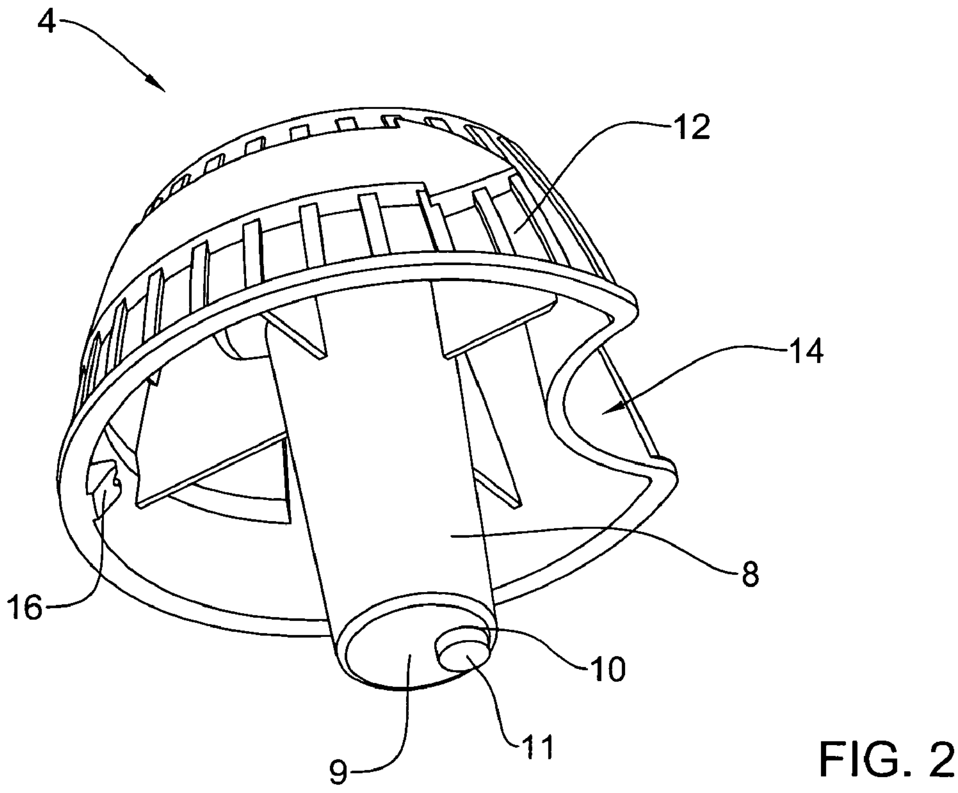
FIG. 2 is a view from below of the sample-containing unit.
Figure 3:
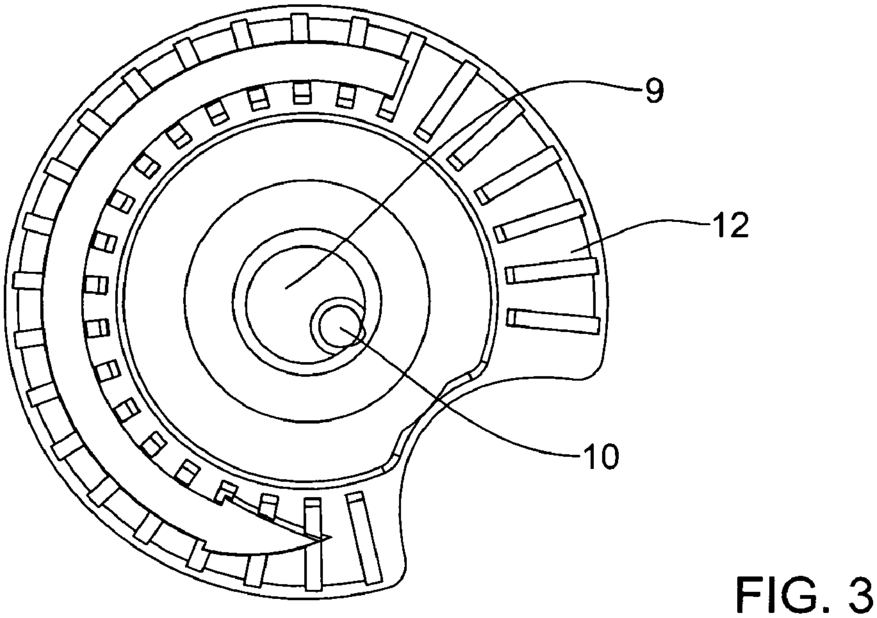
FIG. 3 is an upper view of the sample containing unit.

The sample containing unit (4) comprises the following features as shown in FIG. 2: a conic shaped sample container (8), with a hole (10) sealed by a plug (11) in its bottom wall (9), and being a part of a round shape knob (12), which contains a guiding notch (14); and a limiting protrusion (16) in the lower inner side of the knob, which limits the rotational freedom of the sample container when installed on the housing component. FIG. 3 shows an upper view of the unit showing the sealed hole (10) in the bottom wall (9) of the sample container.

Figure 4:
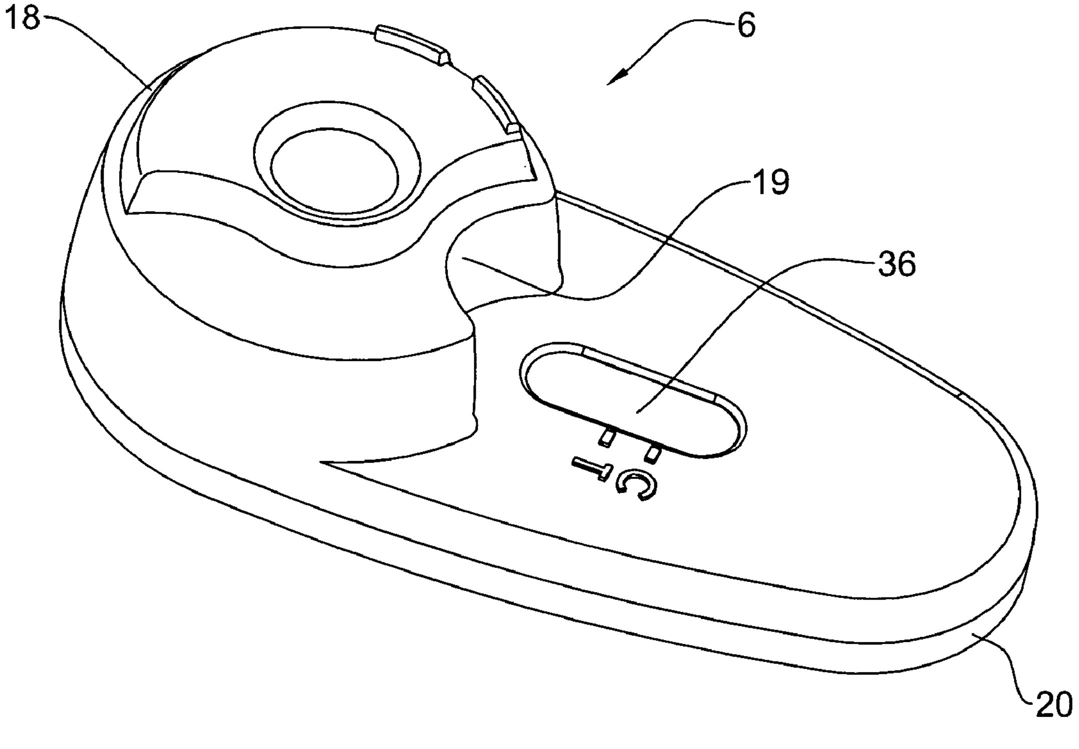
FIG. 4 is a right view of the test strip housing component.
Figure 5:
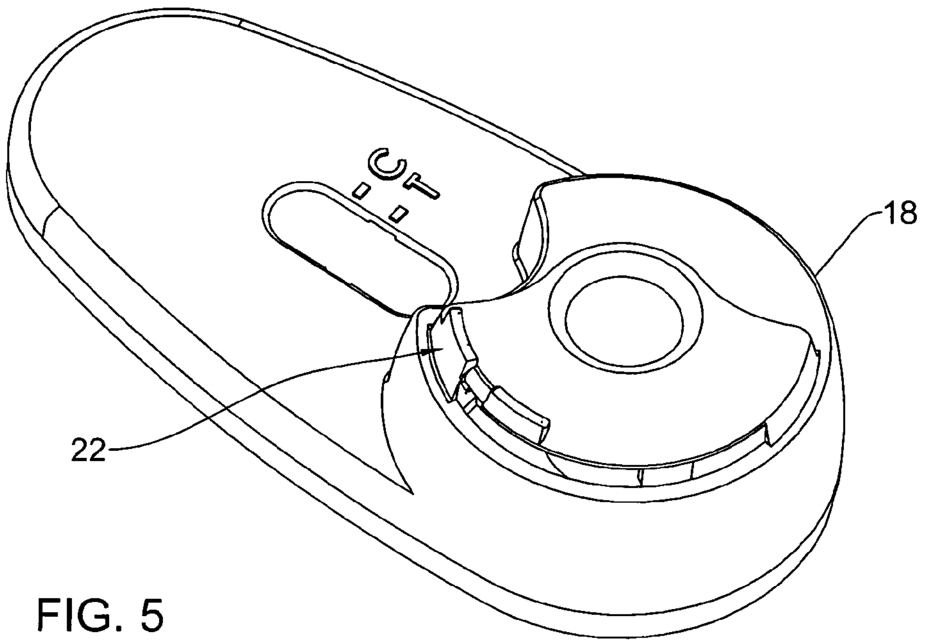
FIG. 5 is a left view of the test strip housing component.

The sample-containing unit is installed on the laterally oriented housing component, which houses the test strip. This housing component (6) comprises 2 parts as shown in FIG. 4: the upper part (18), on which the sample-containing unit is installed; and the bottom part (20), which contains the base support for receiving the test strip. The upper part includes a window (36) for viewing the test results and a notch (19) adjacent one end of the window. FIG. 5 shows a left view of the component. As shown in FIG. 5, the upper part (18) of the strip housing component has an extension (22) intended to facilitate the installment of the sample-containing unit.

Figure 6:
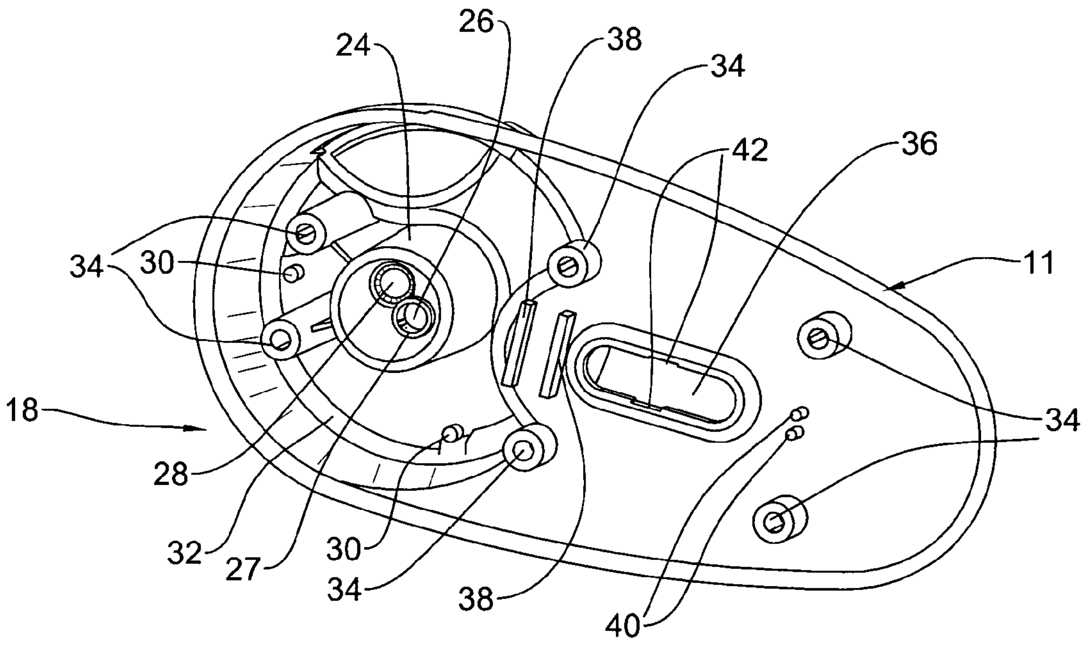
FIG. 6 is a bottom view of the upper part of the housing component.
Figure 7:
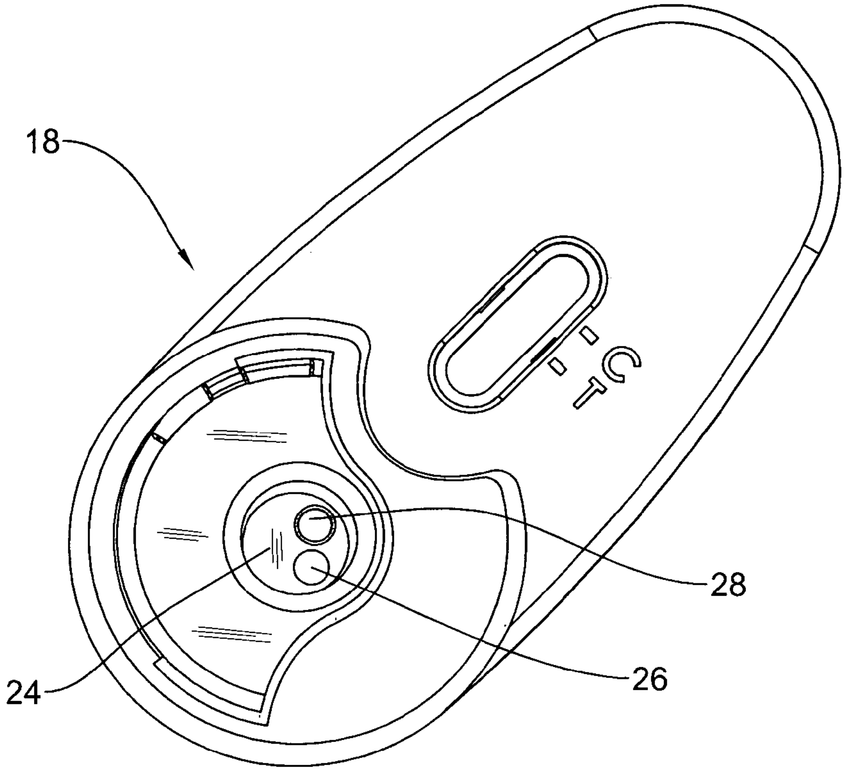
FIG. 7 is an upper view of the upper part of the housing component.

As shown in FIG. 6, the upper part of the test strip housing component contains the following items: a bore (24) to receive the sample container of the sample containing unit; an aperture (26) in the bottom of this bore, located in a specified position, through which the sample reaches the test strip; a ring (27) surrounding the lower side of the aperture (26) and projecting outwardly so that when the upper part of the test strip housing component is engaged with the lower part, the ring presses on the sample application pad of the test strip, thereby ensuring that the sample fluid directly reaches the sample application pad; a cutting arrangement in the form of a conic hole (28), which receives the plug of the hole in the bottom wall of the sample containing unit, and is designed to slice off this plug when the sample containing unit is rotated during operation of the device; two limiting protrusions (30) which restrict the rotation of the sample-containing unit to a limited extent within a limiting groove (32); connecting holes (34) to attach the two parts of the strip housing component; a window opening (36) through which to view test results; press bars (38) which press on the test strip and are located at precise positions over the sample application pad and the conjugate pad of the test strip to ensure uniform contact between the sample application pad and the conjugate pad and between the conjugate pad and the membrane along their entire widths, thus ensuring uniform flow of the sample in the strip; press points (40) located at precise positions which apply pressure to the absorbent pad of the test strip and are intended to ensure uniform contact between the membrane and the absorbent pad along their entire widths, thus ensuring proper flow; and notches (42) in the lateral sides of the window opening to facilitate installation of the window cover in the window opening. FIG. 7 shows an upper view of this upper part.

Figure 8:
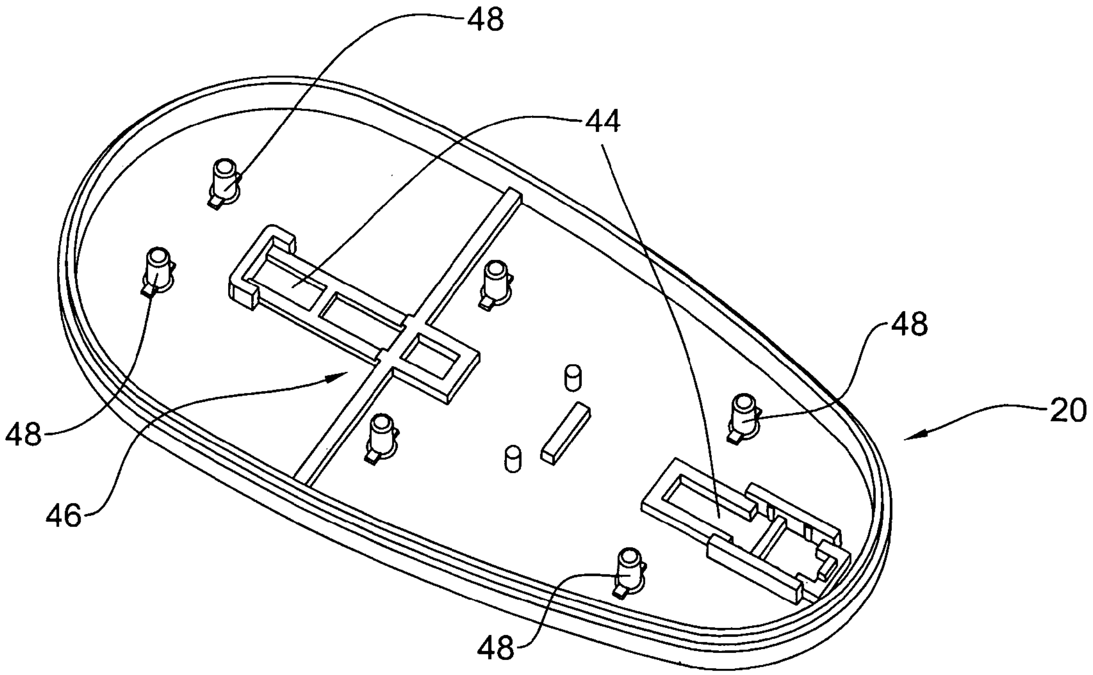
FIG. 8 is an upper view of the bottom part of the housing unit.

As shown in FIG. 8, the bottom part (20) of the test strip housing component contains the following items: a pre-designed base support (44) for the test strip; a dam (46) to create a fluid reservoir intended to prevent flood when the applied volume is higher than the capacity of the strip; and poles (48) to anchor the upper part of the component.

Figure 9:
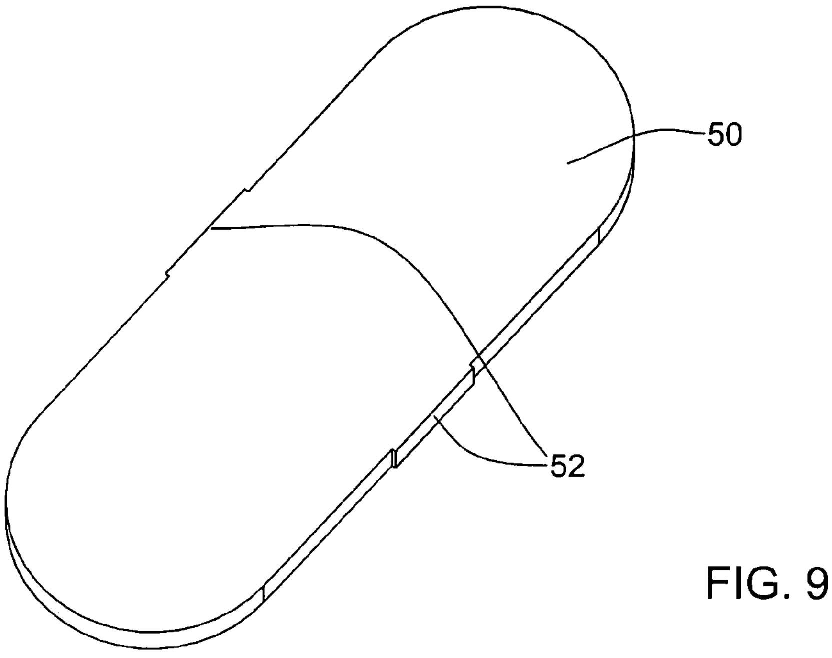
FIG. 9 shows the window cover.
Figure 10:
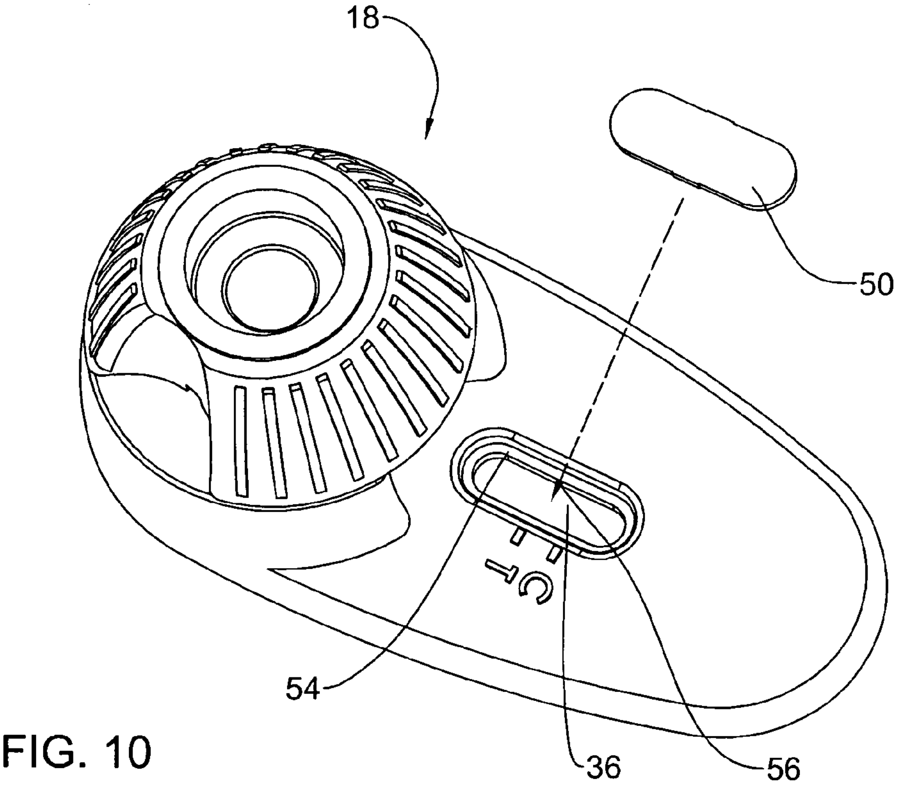
FIG. 10 shows installing the window cover into the upper component of the housing unit.

FIG. 9 shows a transparent window cover (50) with extensions (52) intended to facilitate its installation. FIG. 10 shows the installation of the window cover (50) into the upper component (18) of the housing unit, utilizing a limiting step (54) and notches (56) in the window opening (36) to receive the cover and its extensions.

Figure 11:
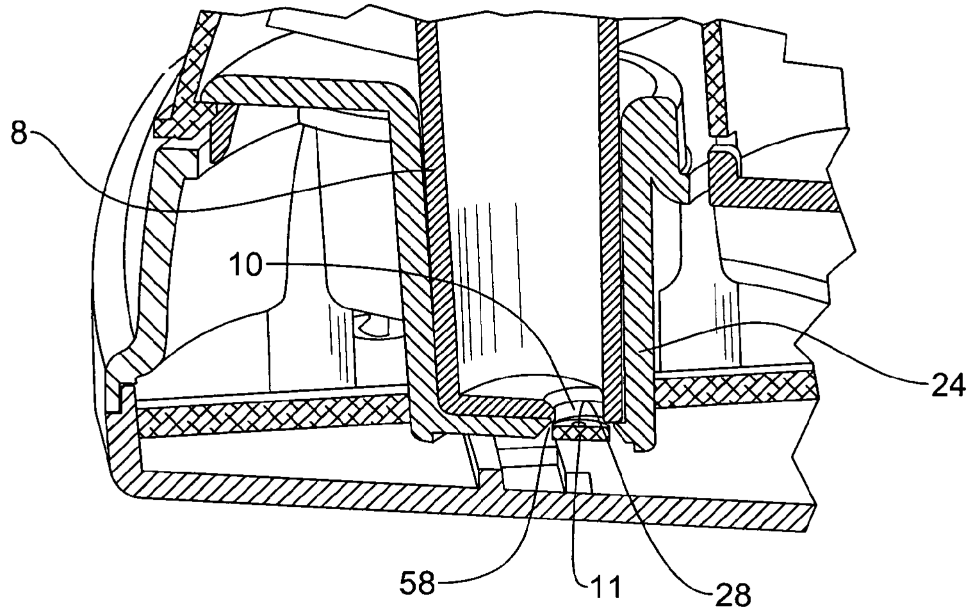
FIG. 11 shows the cutting mechanism of the plug sealing the hole in the sample container.

FIG. 11 demonstrates the mechanism by which the cutting arrangement (58) of the conic hole (28) of the bore (24) slices off the plug (11) which seals the hole (10) in the bottom of the sample container (8).

Figure 12:
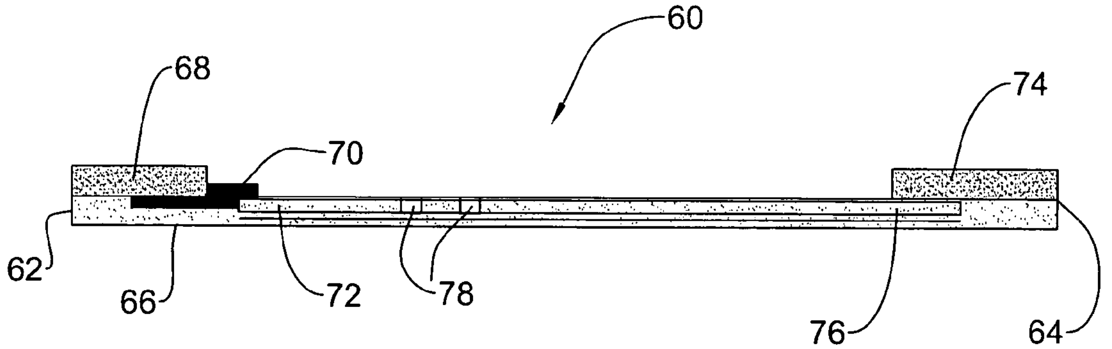
FIG. 12 shows one embodiment of the test strip.

FIG. 12 illustrates one embodiment of a test strip (60) which may be used with the device of the invention, which comprises a first (62) and a second (64) end, and a plastic backing (66) along the length of the strip. On the first end (62) is a sample application pad (68) which is in lateral contact with a conjugate pad (70), which in turn is in lateral contact with a first end of a membrane (72). An absorbent pad (74) is located on the second end (64) of the strip and is in lateral contact with a second end of the membrane (76). The pads and membrane are not necessarily in the same plane, but are in fluid flowing contact with each other. The sample application pad is located under the bottom of the sample container and receives the sample when the hole is revealed. The conjugate pad has impregnated therein an antibody-label conjugate, wherein the antibody specifically binds the analyte. The membrane has a detection zone comprising reagent lines (78) containing immobilized reagent for test and control sites, as is well known in the art.

Operation Procedure

The operation of the device will now be described with reference to the figures. The sample is introduced into the sample container (8) by an appropriate vehicle (e.g. a swab, spoon, stick, etc.). The sample containing unit (4) provides the ability to extract, dilute or treat in any other way the sample before introducing it onto the test strip. For this purpose this unit may contain an extracting or diluting solution, which may be added either prior to the addition of the sample or afterwards. This solution may be stored in the sample containing unit until usage or may be added upon usage.

Once the procedure in the sample container (8) is completed, the whole sample containing unit (4) is turned a quarter of a turn counterclockwise, as shown by the marked arrow on the unit, within a limit set by the groove (32) and the limiting protrusion (16). The significance of this turn is switching on the flow and allowing the immuno-chromatographic test process to begin. As a result of the operating turn, the plug of the hole (11) in the bottom of the sample container is sliced off (FIG. 11) and this hole in its new position is aligned with the aperture (26) existing in the bottom of the bore of the upper part (18) of the strip housing component (6). In this position, both openings are located exactly above and in contact with the sample application pad (68) of the test strip (60), and thus the contents of the sample container are conveyed onto the strip thereby commencing the detection assay, while the volume beyond the capacity of the strip remains in the reservoir created by the dam (46).

The operating turn leads the guiding notch (14) in the sample containing unit (4) to a position in which it is aligned with the corresponding notch (19) located just before the window (36) in the upper part (18) of the strip housing component (6), in order to facilitate viewing the results. This position of aligned notches informs the user that the immuno-chromatographic detection process has begun.

Results are observed in the window following immunoreactivity of the tested solution over the corresponding reagent lines (78) positioned in the detection zone of the test strip (60). Interpretation of results is facilitated by the indications of test (T) and control (C) which appear on the upper surface of the strip housing component next to the window.

The invention claimed is:

1. A device for carrying out a lateral flow assay on a sample comprising:

(a) a sample containing unit comprising a sample container, said sample container being closed off at one end by a bottom wall, said bottom wall having a hole therein sealed by a plug; and (b) a housing located under said sample container and capable of holding a test strip, said sample containing unit and said housing being coupled so as to allow rotation one relative to the other, said housing comprising a slicing arrangement capable of slicing said plug, wherein said housing comprises an upper part which comprises a bore to receive the sample container, said bore having a bottom wall with an aperture therein, through which the sample reaches the test strip when the hole in the bottom wall of said sample containing unit is in alignment with the aperture in the bottom wall of the bore of the upper part of said housing;

wherein rotation of said sample containing unit and said housing one relative to the other results in (1) said slicing arrangement slicing said plug, thereby unplugging the hole in said bottom wall, and (2) the hole becoming aligned with the aperture in the bottom of the bore.

2. The device according to claim 1 wherein said housing further comprises a bottom part which comprises a base support for receiving the test strip.

3. The device according to claim 2 wherein said slicing arrangement is located in the bottom of the bore in the upper part of the housing.

4. The device according to claim 3 wherein said test strip comprises a sample application pad and said aperture in the bottom of the bore is positioned over the sample application pad.

5. The device according to claim 1 wherein the dimensions of the hole in the bottom of the sample container and the aperture in the bottom of the bore are determined by one or more of the following parameters:

(a) the volume of the sample;

(b) the viscosity of the sample;

(c) the dimensions of the test strip; and (d) the fluid capacity of the test strip.

6. The device according to claim 2 wherein said upper part of the housing further comprises pressing members which apply pressure to pre-determined locations on the test strip when said strip is placed in the base support of said bottom part of the housing.

7. The device according to claim 2 wherein said upper part of said housing further comprises a limiting groove and one or more limiting protrusions for limiting rotation of the sample containing unit, and said sample containing unit comprises a corresponding limiting protrusion which is received within the limiting groove when the sample container is installed in the housing.

8. The device according to claim 2 wherein said housing comprises a plurality of base supports for receiving a plurality of test strips.

9. The device according to claim 8 comprising a plurality of sample containers for delivering a sample to each of said test strips.

10. The device according to claim 1 wherein the test strip is capable of detecting a plurality of analytes.

11. The device according to claim 1 wherein said sample container comprises a filtering member to filter the sample prior to its reaching the test strip.

12. The device according to claim 1 wherein an interior wall of the sample container comprises ribs capable of enhancing the mixing efficiency of the sample in the sample container.

13. An apparatus for carrying out a lateral flow assay on one or more samples comprising two or more devices according to claim 1.

14. A device for carrying out a lateral flow assay on a sample comprising:

(a) a sample containing unit comprising a sample container, the sample container being closed off at one end by a bottom wall, and the bottom wall having a hole therein sealed by a plug; and (b) a housing located under the sample container adapted to hold a test strip, the sample containing unit and said housing being coupled so as to allow relative rotation of one to the other, the housing comprising a slicing arrangement capable of slicing off the plug to open the hole, wherein said housing comprises an upper part which comprises a bore to receive the sample container, and said bore has an aperture in the bottom thereof, through which the sample reaches the test strip when the hole in the bottom wall of said sample containing unit is in alignment with the aperture in the bottom wall of the bore of the upper part of said housing;

wherein rotation of the sample containing unit and the housing one relative to the other results in (1) the slicing arrangement slicing off the plug, thereby opening the hole in the bottom wall, and (2) the hole becoming aligned with the aperture in the bottom of the bore.

15. The device of claim 14, wherein said bore is of frustroconical shape to receive the sample container and said bottom part further comprises a base support for receiving the test strip, and wherein said slicing arrangement is located at the bottom of the bore in the upper part of the housing.

* * * * *